US00PP18834P2

(12) United States Plant Patent
Robacker et al.

(10) Patent No.: US PP18,834 P2
(45) Date of Patent: May 27, 2008

(54) ***ABELIA* PLANT NAMED 'RASPBERRY PROFUSION'**

(50) Latin Name: ***Abelia* hybrid**
Varietal Denomination: Raspberry Profusion

(76) Inventors: Carol Robacker, 807 Andrean Way, Peachtree, GA (US) 30269; Sloane M. Scheiber, 2133 Ancient Oak Dr., Ocoee, FL (US) 34761

( * ) Notice: Subject to any disclaimer, the term of this patent is extended or adjusted under 35 U.S.C. 154(b) by 8 days.

(21) Appl. No.: 11/595,432

(22) Filed: Nov. 9, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Wendy C. Haas
(74) *Attorney, Agent, or Firm*—Greenlee Winner and Sullivan, P.C.

(57) ABSTRACT

A new and distinct *Abelia* hybrid which is characterized by compact, upright growth habit, early flowering, and prolific blooming with fragrant, pink purple flowers and showy raspberry red sepals.

3 Drawing Sheets

Figure 1:
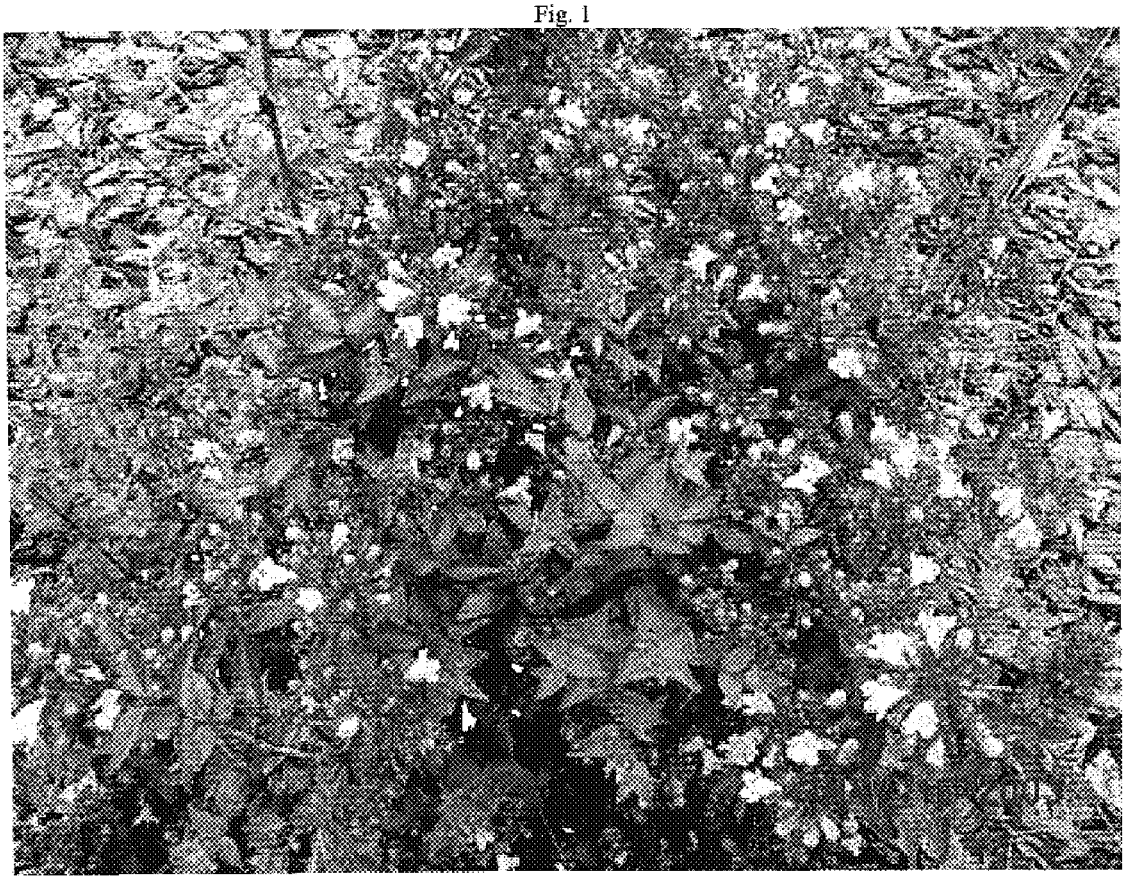

Botanical classification: *Abelia* hybrid.
Varietal denomination: 'Raspberry Profusion'.

BACKGROUND OF THE INVENTION

The present invention relates to a new and distinct cultivar of the ornamental flowering shrub *Abelia,* hereinafter referred to by the varietal denomination 'Raspberry Profusion'. 'Raspberry Profusion' originated from an interspecific cross made in 1998 between the cultivar 'Edward Goucher' (unpatented) and *Abelia chinensis* R. Br. Seeds from this cross were sown in 1999, and eleven seedlings were obtained. These seedlings were planted in a field plot in Griffin, Ga. in the fall of 1999 and were evaluated for three years for flowering and foliage characteristics, plant form and height, cold hardiness and drought tolerance. Plant 99-6-9 was selected among these plants, and assigned the name 'Raspberry Profusion'.

'Raspberry Profusion' forms a dense compact shrub. A 4-year old, unpruned, field grown plant measured 145 cm tall and 185 cm wide. Check cultivars 'Francis Mason' (unpatented) (132×137 cm) and 'Rose Creek' (unpatented) (142×198 cm) were similar in size, whereas 'Compacta' (unpatented) (195×240 cm), 'Golden Glow' (unpatented) (175×211 cm) and 'Little Richard' (unpatented) (165×244 cm) were significantly larger.

The foliage of 'Raspberry Profusion' is medium to dark green, although the glossy leaves are largely obscured by the heavy flowering. The plant is mostly deciduous in winners in USDA Zone 7. 'Raspberry Profusion' is an early bloomer, beginning in mid May, and is a prolific bloomer with fragrant, pink flowers and showy, raspberry colored sepals. Large compound panicles of flowers and sepals cover the plant. Terminal shoot panicles average 9 cm long by 5 cm wide axillary panicles average 7 cm to 3.5 cm.

Laboratory evaluations of cold hardiness in Griffin, Ga. during the winter of 2003–04 revealed a mid-winter hardiness of −18 to −21° C., similar to the check cultivars 'Francis Mason' and 'Prostrata' (unpatented), and 3 to 4° C. more hardy than 'Canyon Creek' (unpatented) and 'Rose Creek'. Plants grown in Blairsville and Griffin, Ga. during the 2003–04 winter had no damage.

'Raspberry Profusion' has drought tolerance typical of *Abelia,* and once established it continues to grow and bloom without irrigation, although leaf drop occurs in summer and fall under drought stress, similar to the check cultivars.

SUMMARY OF THE INVENTION

Plants of the cultivar 'Raspberry Profusion' have not been observed under all possible environmental conditions. The phenotype may vary somewhat with variations in environment such as light-intensity, temperature and cultural conditions, however without any variance in genotype.

The following characteristics have been consistently observed and, to the best knowledge of the inventor, their combination forms the unique characteristics of 'Raspberry Profusion' as a new and distinct cultivar.

1. Compact dense growth habit with periodic pruning.
2. Early flowering in mid May, only 'Edward Goucher' blooms this early.
3. Very prolific bloomer with large compound panicles on both terminal and axillary shoots covering the whole plant.
4. Large, raspberry red, showy sepals, 5 per floret, which remain on the plant from late spring through summer.

The inventor is not aware of any similar cultivars available for direct comparison with 'Raspberry Profusion'. 'Edward Goucher' blooms early, but does not have the large showy panicles of pink flowers and raspberry colored sepals of 'Raspberry Profusion'. *Abelia chinensis* has compound panicles, but the flowers are white or pale pink and the sepals green with a pale pink blush, and it blooms mid to late summer.

'Raspberry Profusion' is readily propagated through cuttings. Six-inch cuttings, collected in August, root well in peat-perlite mix under mist. Asexual propagation at Griffin, Ga. since 2001 has shown that the unique characteristics of this new cultivar are stable and reproduced true to type in successive generations.

BRIEF DESCRIPTION OF PHOTOGRAPHS

The accompanying colored photographs illustrate the characteristics of the new cultivar, showing the colors as true as it is reasonably possible to obtain in colored reproductions of this type. Colors in the photograph may differ from the color values listed in the detailed botanical description which accurately describes the colors of the new *Abelia*.

FIG. 1. Early blooming plant, taken May 16, 2003.

Figure 2:
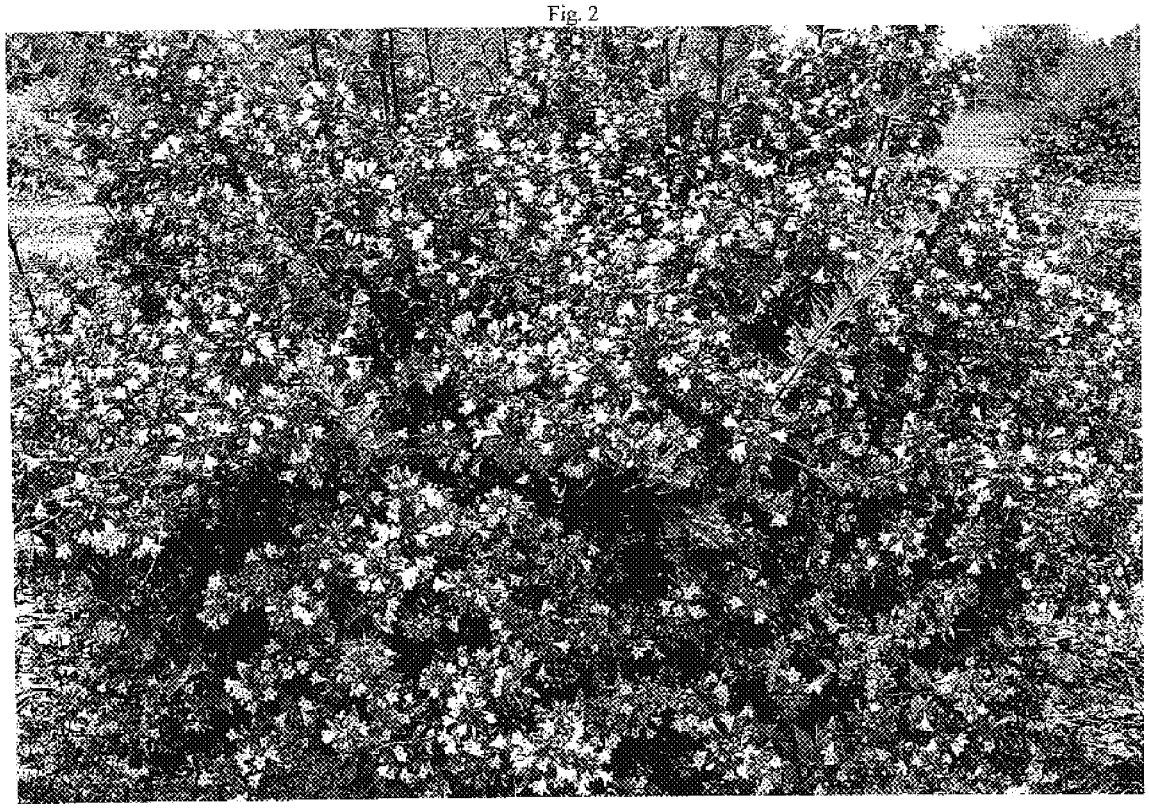

FIG. 2. Prolific flowering, Jun. 17, 2005.

Figure 3:
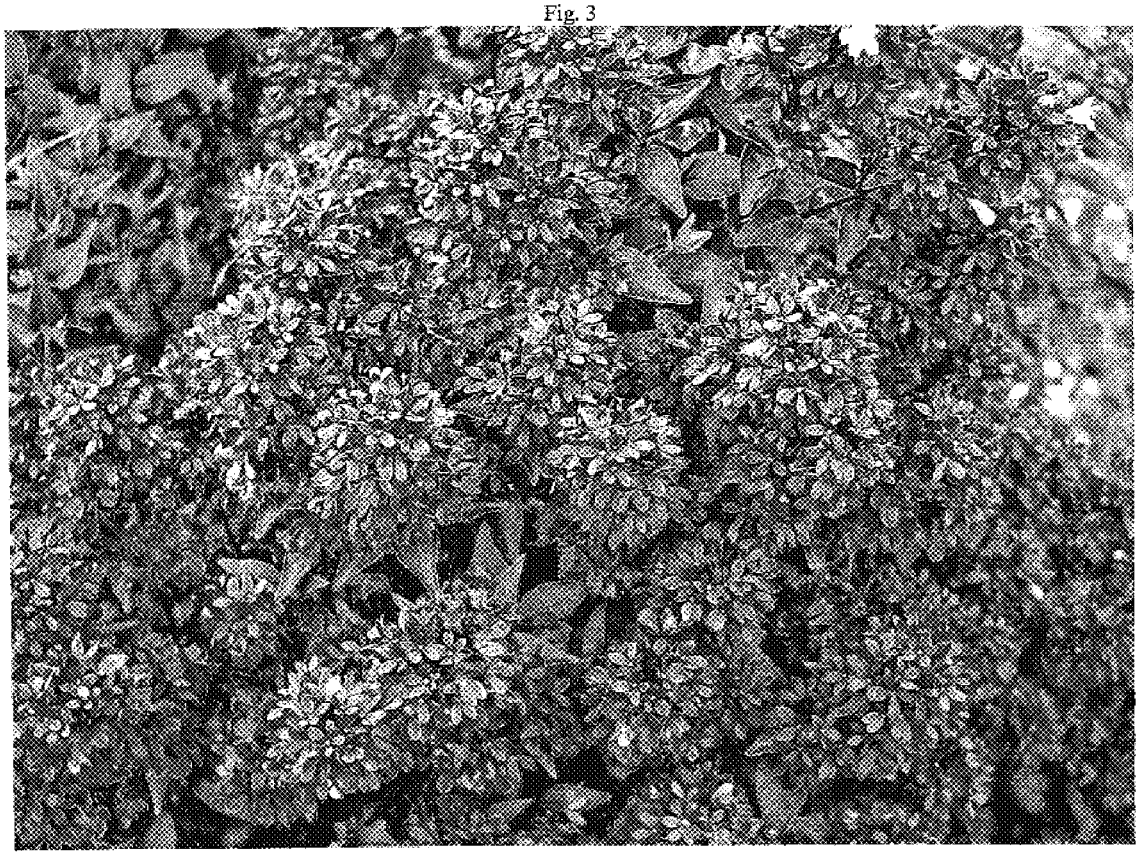

FIG. 3. Plant showing deep raspberry colored sepals, taken Jul. 28, 2005.

DETAILED BOTANICAL DESCRIPTION

The botanical description of 'Raspberry Profusion' is based on 4-year old plants growing in the field in Griffin, Ga. (USDA Zone 7b). Colors are based on The Royal Horticultural Color Chart (2001). Unless otherwise indicated, measurements, based on 10 to 20 samples, were taken in July/August of 2005.

The plant has a spreading upright habit with medium texture of branching, attaining an average grown height of 145 cm and width of 185 cm after 4-years unpruned growth in the field.

Current year stems are round, 1.7 mm in diameter, puberulent with a mix of short and longer fine hairs, some curved, and vary from Greyed-Orange 165B to Greyed-Red 178A in color. The stems show no exfoliation. The average internode length is 26 mm.

Older stems are round, up to 12 mm in diameter and vary from Greyed-Orange N170A to Orange-White 159A with Greyed-Orange 177B striations with maturation. Mature stems are somewhat rough and striated, with some exfoliation.

The vegetative buds are opposite or ternary, valvate, lanceolate in shape, 1.5 mm long by 2 mm wide with 2 scales Greyed-Purple 183A in color. There are 2 single (opposite) or 3 single (ternary) buds at each node, at 45° to the stem.

The mature leaf is 3.1 cm long by 1.7 cm wide. It is lanceolate in shape with a rounded acute apex, a rounded, equilateral base and crenate margin. The upper surface has scattered, tiny hairs, and the lower surface is glabrous. There is a concentration of hairs along the midvein and some large axillary vein, with a single row of hairs around the leaf margin. The leaves are slightly waxy, up to 0.4 mm thick and opposite, trifoliate or occasionally quaternary on the stem. The venation is simple alternate and the veins are Yellow-Green 147D.

The emerging leaves (May) are Yellow-Green 144A blushed with Greyed-Red 182B on the upper surface, and Yellow-Green 145B on the lower surface. In summer (August) the leaves are Yellow-Green 147A on the upper and Yellow-Green 144A on the lower surface. In the fall (September) the upper surface is Green 137A with lower surface, Green 138B.

The petiole is slightly curved and concaved, 3 mm in length and 1 mm in diameter, with sparse pubescence along the edges and scattered short hairs on the back, and Yellow-Green 143C in color.

The flower buds are elongated teardrop in shape, 9 mm long by 4 mm wide, covered in short glandular hairs, and Red-Purple 63C in color. The buds show from mid May till frost.

The inflorescences are compound panicles, mostly terminal with some axillary. The compound panicles range from 12 to 28 cm in length by 8 to 18 cm in width, making up from 4 to 15 sub panicles, with terminal sub panicels averaging 9 cm by 5 cm, and axillary sub panicles 7 cm by 3.5 cm. At full bloom the inflorescence is Purple 75B, fading to Red-Purple 69D. There are 250–750 individual flowers per inflorescence, all at different stages of development.

The peduncle is covered in short curved hairs, with bracteoles, and is Red-Purple 58A in color.

The flower is funnel shaped, slightly tubular and gamopetalous, 12 mm long by 8 mm wide. The petals have 5 lobes, which are rounded and slightly curled. The margin is slightly curled. It has short curled hairs, slightly glandular. At peak of bloom, the color of the upper surface is Purple 75B and the lower surface is Red-Purple N74D.

The pedicels are 1 mm long, with scattered hairs, are Red-Purple 58A in color.

There are mostly 5 sepals, sometimes including 1 cleft sepal. They are 5 mm long by 3 mm wide, oval to elliptic in shape with rounded apex, equilateral base and entire margin. They are lightly scattered with hairs, smooth texture and are Red-Purple 59D on both upper and lower surfaces.

There are 4 stamens.

The anther is dorsifixed, revolute, 1 mm long by 0.5 mm wide and Yellow-White 158D in color.

The filament is 10 mm long and 0.4 mm wide and has scattered hairs towards the base. The color is White N155B.

The pollen color is White N155B.

The pistil is monostylus, free in shape, 18 mm long by 1 mm wide and mostly glabrous.

The stigma is circular, slightly doomed in shape, glabrous, and is Orange-White 159C in color.

The style is tubular in shape, 13 mm long, mostly glabrous, and White 155B in color.

The single, epigynous inferior ovary is oval in shape, covered in short curved hairs.

The fruit is an achene, a grooved cylindrical capsule in shape, 6 mm long and 1.5 mm wide with 1 carpel. The color matures from Red-Purple 59D and Yellow-Green 145C to Greyed-Orange 174A.

The seed are cylindrical, grooved longitudinally, 6 mm long by 1.5 mm wide, covered in short curved hairs, and Brown 200D in color.

No insect or disease problems have been noted in container plants maintained outside the greenhouse, or in field grown plants.

We claim:

1. A new and distinct cultivar of *Abelia* plant named 'Raspberry Profusion', substantially as illustrated and described.

* * * * *